(12) United States Patent
Ichikawa

(10) Patent No.: US 9,517,054 B2
(45) Date of Patent: Dec. 13, 2016

(54) ULTRASOUND OBSERVATION APPARATUS, METHOD FOR OPERATING ULTRASOUND OBSERVATION APPARATUS, AND COMPUTER-READABLE RECORDING MEDIUM

(71) Applicant: OLYMPUS CORPORATION, Tokyo (JP)

(72) Inventor: Junichi Ichikawa, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/138,331

(22) Filed: Apr. 26, 2016

(65) Prior Publication Data

US 2016/0235390 A1 Aug. 18, 2016

Related U.S. Application Data

(63) Continuation of application No. PCT/JP2015/062607, filed on Apr. 24, 2015.

(30) Foreign Application Priority Data

Jun. 24, 2014 (JP) .................................. 2014-129677

(51) Int. Cl.
*A61B 8/08* (2006.01)
*A61B 8/14* (2006.01)
*A61B 8/00* (2006.01)

(52) U.S. Cl.
CPC ................. *A61B 8/481* (2013.01); *A61B 8/14* (2013.01); *A61B 8/4444* (2013.01);
(Continued)

(58) Field of Classification Search
CPC ........... A61B 8/481; A61B 8/14; A61B 8/461; A61B 8/54
See application file for complete search history.

(56) References Cited

FOREIGN PATENT DOCUMENTS

| JP | 2007-082649 A | 4/2007 |
|---|---|---|
| JP | 2011-120707 A | 6/2011 |
| WO | WO 2012/011414 A1 | 1/2012 |

OTHER PUBLICATIONS

International Search Report dated Jul. 28, 2015 issued in PCT/JP2015/062607.

(Continued)

*Primary Examiner* — Joseph M Santos Rodriguez
(74) *Attorney, Agent, or Firm* — Scully, Scott, Murphy & Presser, P.C.

(57) ABSTRACT

An ultrasound observation apparatus includes: an analysis unit that analyzes a frequency of a signal using a parameter that differs depending on presence or absence of a contrast agent in a specimen to calculate a frequency spectrum, the signal being generated based on an echo signal reflected from the specimen; a calculation unit configured to calculate a feature of the frequency spectrum; a generating unit that generates feature image data for displaying visual information related to the feature in a display pattern that differs depending on the presence or absence of the contrast agent in the specimen; a determination unit that determines the presence or absence of the contrast agent using the frequency spectrum and information on a known frequency spectrum in the presence of the contrast agent in the specimen; and a control unit that changes a setting of the parameter in accordance with a result of the determination.

10 Claims, 12 Drawing Sheets

(52) U.S. Cl.
CPC ............ *A61B 8/4483* (2013.01); *A61B 8/461* (2013.01); *A61B 8/5207* (2013.01); *A61B 8/54* (2013.01)

(56) References Cited

OTHER PUBLICATIONS

Japanese Office Action dated Nov. 17, 2015 issued in JP 2015-542896.
Japanese Office Action dated Jan. 19, 2016 issued in JP 2015-542896.

| | ABSENCE OF CONTRAST AGENT | PRESENCE OF CONTRAST AGENT |
|---|---|---|
| FREQUENCY BAND | $f_L$ TO $f_H$ | $f_L'$ TO $f_H'$ |

ULTRASOUND OBSERVATION APPARATUS, METHOD FOR OPERATING ULTRASOUND OBSERVATION APPARATUS, AND COMPUTER-READABLE RECORDING MEDIUM

CROSS REFERENCES TO RELATED APPLICATIONS

This application is a continuation of PCT international application Ser. No. PCT/JP2015/062607, filed on Apr. 24, 2015 which designates the United States, incorporated herein by reference, and which claims the benefit of priority from Japanese Patent Application No. 2014-129677, filed on Jun. 24, 2014, incorporated herein by reference

BACKGROUND

1. Technical Field

The disclosure relates to an ultrasound observation apparatus for observing a tissue of a specimen using an ultrasound wave, a method for operating the ultrasound observation apparatus, and a computer-readable recording medium.

2. Related Art

As a technique for observing a tissue of a specimen using an ultrasound wave, there is a known technique for performing frequency analysis for an electrical echo signal obtained by converting an ultrasound echo from a specimen, and generating a feature image to which feature of a frequency spectrum obtained as the result of the analysis are added as visual information (for example, refer to WO 2012/011414 A).

SUMMARY

In some embodiments, an ultrasound observation apparatus includes: a frequency analysis unit configured to analyze a frequency of a signal using a parameter that differs depending on presence or absence of a contrast agent in a specimen to calculate a frequency spectrum, the signal being generated based on an echo signal obtained by converting an ultrasound echo, which is an ultrasound wave transmitted to and reflected from the specimen, into an electric signal; a feature calculation unit configured to calculate a feature of the frequency spectrum calculated by the frequency analysis unit; a feature image data generating unit configured to generate feature image data for displaying visual information related to the feature calculated by the feature calculation unit in a display pattern that differs depending on the presence or absence of the contrast agent in the specimen; a storage unit configured to store, as reference spectrum information, information on a known frequency spectrum in the presence of the contrast agent in the specimen; a determination unit configured to determine the presence or absence of the contrast agent using the frequency spectrum and the reference spectrum information; and a control unit configured to change a setting of the parameter in accordance with a determination result by the determination unit.

In some embodiments, provided is a method for operating an ultrasound observation apparatus that transmits an ultrasound wave to a specimen and receives an ultrasound echo reflected from the specimen to convert the ultrasound echo into an electrical echo signal. The method includes: analyzing, by a frequency analysis unit, a frequency of a signal generated based on the echo signal, using a parameter that differs depending on presence or absence of a contrast agent in the specimen to calculate a frequency spectrum; calculating, by a feature calculation unit, a feature of the frequency spectrum; generating, by a feature image data generating unit, feature image data for displaying visual information related to the feature in a display pattern that differs depending on the presence or absence of the contrast agent in the specimen; determining, by a determination unit, the presence or absence of the contrast agent using the frequency spectrum and reference spectrum information that is information on a known frequency spectrum in the presence of the contrast agent in the specimen; and changing, by a control unit, a setting of the parameter in accordance with a result of determining the presence or absence of the contrast agent.

In some embodiments, a non-transitory computer-readable recording medium with an executable program stored thereon is provided. The program instructs an ultrasonic observation apparatus that transmits an ultrasound wave to a specimen and receives an ultrasound echo reflected from the specimen to convert the ultrasound echo into an electrical echo signal, to execute: analyzing, by a frequency analysis unit, a frequency of a signal generated based on the echo signal, using a parameter that differs depending on presence or absence of a contrast agent in the specimen to calculate a frequency spectrum; calculating, by a feature calculation unit, a feature of the frequency spectrum; generating, by a feature image data generating unit, feature image data for displaying visual information related to the feature in a display pattern that differs depending on the presence or absence of the contrast agent in the specimen; determining, by a determination unit, the presence or absence of the contrast agent using the frequency spectrum and reference spectrum information that is information on a known frequency spectrum in the presence of the contrast agent in the specimen; and changing, by a control unit, a setting of the parameter in accordance with a result of determining the presence or absence of the contrast agent.

The above and other features, advantages and technical and industrial significance of this invention will be better understood by reading the following detailed description of presently preferred embodiments of the invention, when considered in connection with the accompanying drawings.

DETAILED DESCRIPTION

Hereinafter, modes for carrying out the invention (hereinafter referred to as "embodiment(s)") will be described with reference to the accompanying drawings.

First Embodiment

Figure 1:
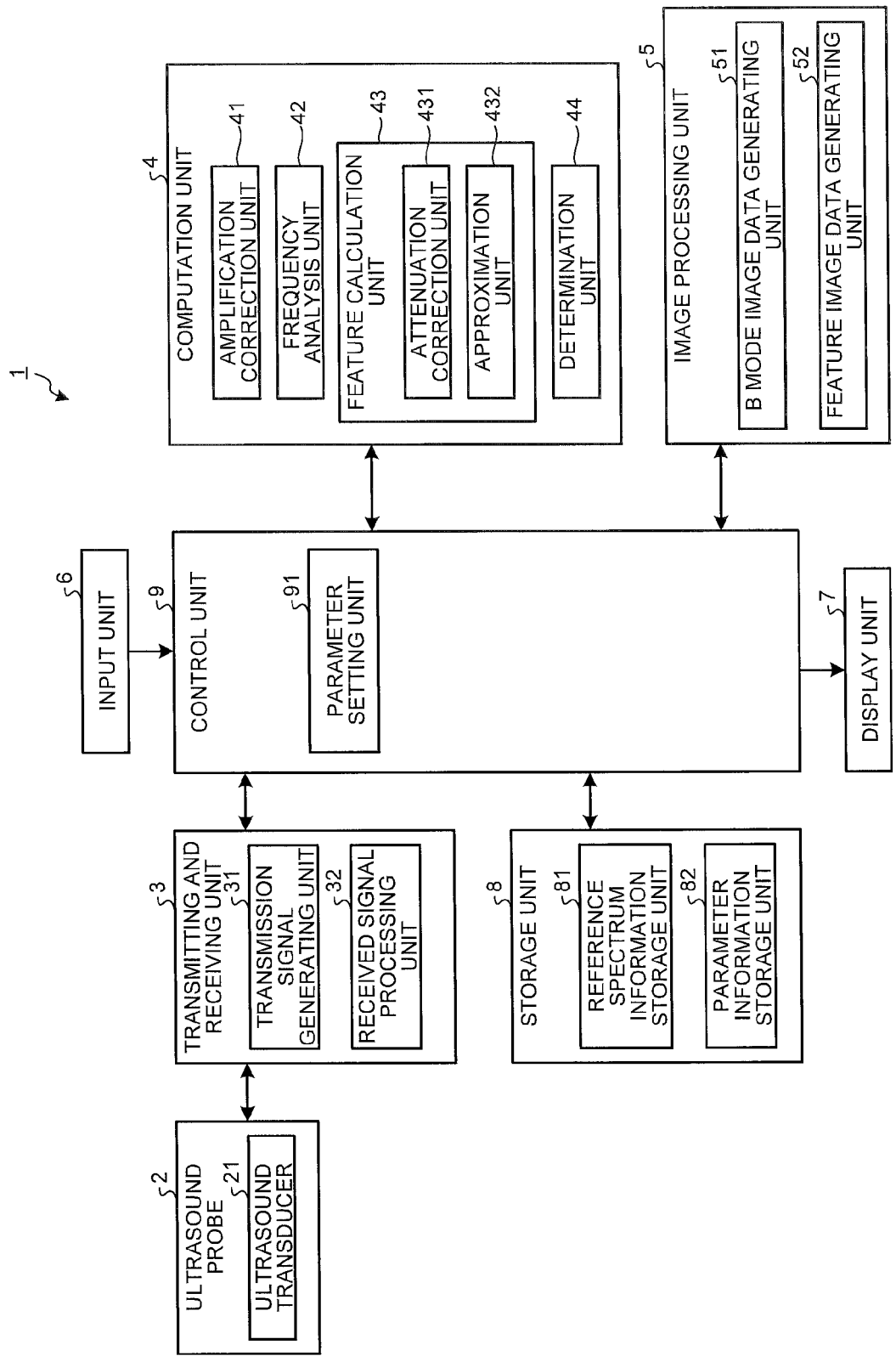
FIG. 1 is a block diagram illustrating a configuration of an ultrasound observation apparatus according to a first embodiment of the present invention.

FIG. 1 is a block diagram illustrating a configuration of an ultrasound observation apparatus according to a first embodiment of the present invention. An ultrasound observation apparatus 1 illustrated in FIG. 1 is an apparatus for observing a specimen to be diagnosed using an ultrasound wave.

The ultrasound observation apparatus 1 includes an ultrasound probe 2, a transmitting and receiving unit 3, a computation unit 4, an image processing unit 5, an input unit 6, a display unit 7, a storage unit 8, and a control unit 9. The ultrasound probe 2 outputs an ultrasound pulse to the outside and receives an ultrasound echo reflected from the outside.

The transmitting and receiving unit 3 transmits and receives an electric signal to and from the ultrasound probe 2. The computation unit 4 performs a predetermined arithmetic operation on an electrical echo signal obtained by converting an ultrasound echo to an electric signal. The image processing unit 5 generates image data corresponding to an electrical echo signal. The input unit 6 is realized by using a user interface such as a keyboard, a mouse, and a touch panel to receive input of various types of information. The display unit 7 is realized by using a display panel made of, for example, liquid crystal or an organic electro luminescence (EL) material to display various types of information including an image generated by the image processing unit 5. The storage unit 8 stores therein various types of information required for ultrasound observation. The control unit 9 controls operation of the ultrasound observation apparatus 1.

The ultrasound observation apparatus 1 includes the ultrasound probe 2 and a processing device (processor). The ultrasound probe 2 is provided with an ultrasound transducer 21 and detachably connected to the processing device. The above-mentioned units except for the ultrasound probe 2 are provided in the processing device. The ultrasound probe 2 as used herein may be formed in any of: a form of an extracorporeal probe that radiates ultrasound from a surface of a living body; a form of a miniature ultrasound probe equipped with an elongated insertion part to be inserted into a lumen such as an alimentary canal, a biliopancreatic duct, and a blood vessel; and a form of an ultrasound endoscope that is an intraluminal ultrasound probe further equipped with an optical system. Among them, in the form of the intraluminal ultrasound probe such as the ultrasound endoscope, the ultrasound transducer 21 is provided at a distal end side of the insertion part of the intraluminal ultrasound probe, and the intraluminal ultrasound probe is detachably connected to the processing device at a proximal end side of the intraluminal ultrasound probe.

The ultrasound probe 2 has the ultrasound transducer 21 that converts an electrical pulse signal received from the transmitting and receiving unit 3 to an ultrasound pulse (acoustic pulse) and converts an ultrasound echo reflected from an external specimen to an electrical echo signal. The ultrasound probe 2 may be configured to cause the ultrasound transducer 21 to perform scanning mechanically. Alternatively, the ultrasound probe 2 may be configured such that a plurality of elements is provided as the ultrasound transducer 21 in the form of an array, and elements related to transmitting and receiving are switched electronically or transmitting and receiving by each element is delayed, thereby causing the ultrasound transducer 21 to perform scanning electronically. In the first embodiment, any of a plurality of kinds of ultrasound probes 2 which are different from one another can be selected and used as the ultrasound probe 2.

The transmitting and receiving unit 3 includes a transmission signal generating unit 31 and a received signal processing unit 32. The transmission signal generating unit 31 generates an electrical pulse signal based on a predetermined waveform and transmission timing and outputs the electrical pulse signal to the ultrasound probe 2. The received signal processing unit 32 receives the electrical echo signal from the ultrasound probe 2 and performs a predetermined signal process for the echo signal.

The received signal processing unit 32 performs, for the electrical echo signal, a signal process such as sensitivity time control (STC) correction as an amplification process, filtering, A/D conversion, and delay addition, and generates a digital radio frequency (RF) signal in a time domain in each transmission direction of ultrasound. Hereinafter, the digital RF signal in each transmission direction will be referred to as sound ray data. When the ultrasound probe 2 is configured to cause the ultrasound transducer 21, i.e. the plurality of elements provided in the form of an array, to perform the scanning electronically, the transmitting and receiving unit 3 has a multichannel circuit for combining beams corresponding to the plurality of elements.

Figure 2:
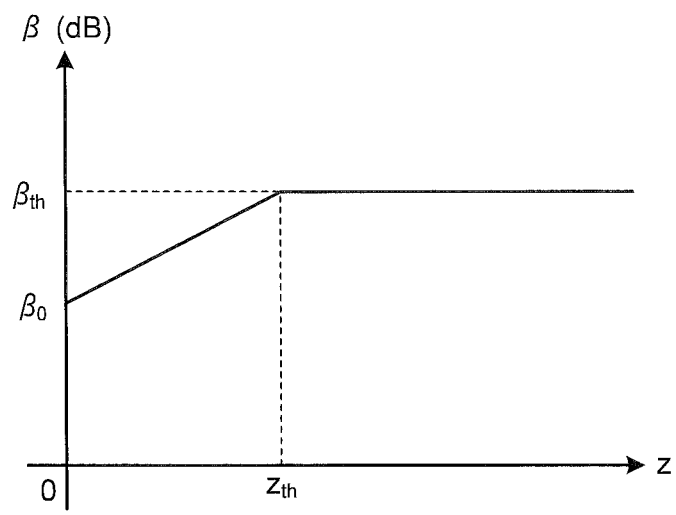
FIG. 2 is a diagram illustrating a relation between a reception depth and an amplification factor in an amplification process performed by a received signal processing unit of the ultrasound observation apparatus according to the first embodiment of the present invention.

FIG. 2 is a diagram illustrating a relation between a reception depth and an amplification factor in the STC correction process performed by the received signal processing unit 32. The reception depth z illustrated in FIG. 2 is an amount that is calculated based on the time that has elapsed since the point of starting to receive ultrasound. As illustrated in FIG. 2, when the reception depth z is less than a threshold value $z_{th}$, the amplification factor β (dB) linearly increases from $β_0$ to $β_{th}$ ($>γ_0$) as the reception depth z increases. When the reception depth z is equal to or greater than the threshold value $z_{th}$, the amplification factor β (dB) is a constant value $β_{th}$. The threshold value $z_{th}$ is such a value that an ultrasound signal received from a specimen is attenuated almost completely and noise becomes dominant. More generally, when the reception depth z is less than the threshold value $z_{th}$, the amplification factor β is only required to monotonously increase as the reception depth z increases.

The computation unit 4 has an amplification correction unit 41, a frequency analysis unit 42, a feature calculation unit 43, and a determination unit 44. The amplification correction unit 41 performs amplification correction for a digital RF signal so that the amplification factor β is constant regardless of the reception depth. The frequency analysis unit 42 calculates a frequency spectrum by subjecting the digital RF signal that has undergone the amplification correction to fast Fourier transform (FFT) to perform frequency analysis. The feature calculation unit 43 calculates a feature of the frequency spectrum. The determination unit 44 determines the presence or absence of a contrast agent for ultrasound in a specimen by using the frequency spectrum calculated by the frequency analysis unit 42 and reference spectrum information stored in the storage unit 8. The reference spectrum information as used herein is information of a known frequency spectrum in the presence of a contrast agent in a specimen.

The computation unit 4 is realized by using a central processing unit (CPU) and various types of arithmetic circuits or the like. A digital RF signal to be processed by the computation unit 4 is stored in advance in the storage unit 8 for generation of a feature image to which visual information related to the feature is added.

Figure 3:
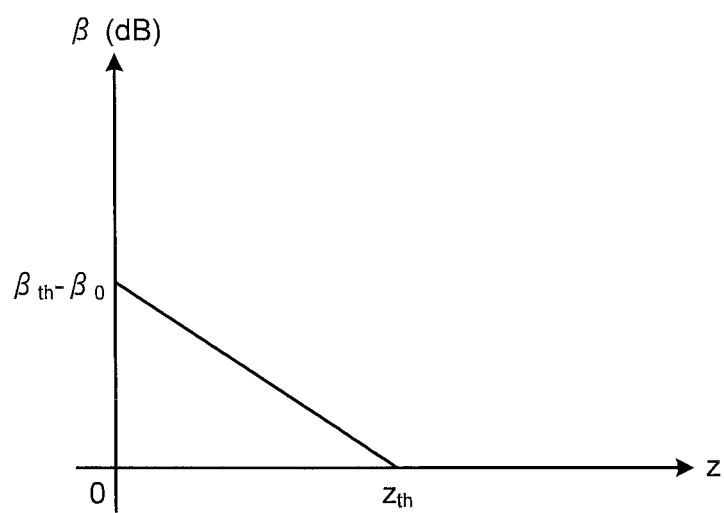
FIG. 3 is a diagram illustrating a relation between a reception depth and an amplification factor in an amplification process performed by an amplification correction unit of the ultrasound observation apparatus according to the first embodiment of the present invention.

FIG. 3 is a diagram illustrating a relation between a reception depth and an amplification factor in an amplification process performed by the amplification correction unit 41. As illustrated in FIG. 3, when the reception depth z is zero, the amplification factor β (dB) in the amplification process performed by the amplification correction unit 41 is a maximum value $β_{th}$–$β_0$, and linearly decreases as the reception depth z moves from zero to a threshold value $z_{th}$. When the reception depth z is equal to or greater than the threshold value $z_{th}$, the amplification factor β (dB) is zero. When the amplification correction unit 41 performs the amplification correction for the digital RF signal in accordance with the amplification factor thus defined, it is possible to offset the influence of the STC correction performed by the received signal processing unit 32 and output a signal having a constant amplification factor $β_{th}$. Needless to say, the relation between the reception depth z and the amplification factor β managed by the amplification correction unit 41 differs depending on the relation between the reception depth and the amplification factor in the received signal processing unit 32.

The reason for performing the above-mentioned amplification correction will be described. The STC correction is such a correction process as to amplify amplitude of an analog signal waveform uniformly over all frequency bands while causing the amplification factor to monotonously increase with respect to the depth, thereby eliminating the influence of the attenuation from the amplitude of the analog signal waveform. Therefore, in a case where a B-mode image using amplitude of an echo signal is generated, and in a case where a uniform tissue has been scanned, a brightness value becomes constant regardless of the depth by performing the STC correction. In other words, an effect of eliminating the influence of the attenuation from a B-mode brightness value can be obtained. On the other hand, in a case where the result of calculating and analyzing the frequency spectrum of the ultrasound is used as described in the first embodiment, the influence of the attenuation accompanying the propagation of the ultrasound cannot necessarily be accurately eliminated even by the STC correction. This is because an attenuation amount differs depending on the frequency as represented by formula (1) described later while the amplification factor of the STC correction varies only with respect to a distance and does not vary and stays constant with respect to the frequency. A method for eliminating the influence of the attenuation in consideration of the frequency dependence of the attenuation amount will be described as an "attenuation correction process" later in FIG. 6 and step S12 of FIG. 8.

In order to solve the above-mentioned problem, namely the problem that the influence of the attenuation accompanying the propagation of the ultrasound cannot necessarily be accurately eliminated even by the STC correction in a case where the result of calculating and analyzing the frequency spectrum of the ultrasound is used, a possible solution is to output a received signal that has undergone the STC correction when generating a B-mode image, and to perform new transmission different from transmission for generating the B-mode image when generating an image based on the frequency spectrum to output a received signal that has not undergone the STC correction. However, this solution has a problem that a frame rate of image data to be generated based on the received signal is reduced.

In order to address this problem, in the first embodiment, the amplification factor is corrected by the amplification correction unit 41 to eliminate the influence of the STC correction from the signal that has undergone the STC correction for the B-mode image while maintaining the frame rate of the image data to be generated.

The frequency analysis unit 42 subjects an amplitude data group to the fast Fourier transform to calculate frequency spectra at a plurality of positions (data positions) on a sound ray. The amplitude data group is sampled, at predetermined time intervals, from each sound ray (line data) of a signal obtained by subjecting a digital RF signal that is based on an echo signal to the amplification correction.

Figure 4:
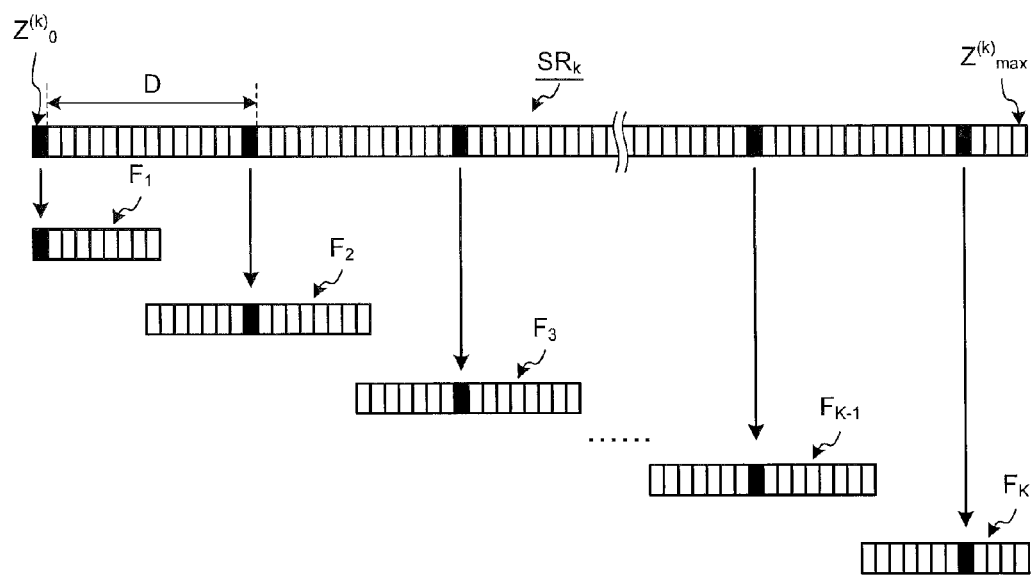
FIG. 4 is a diagram schematically illustrating a data array in a single sound ray of an ultrasound signal.

FIG. 4 is a diagram schematically illustrating a data array in a single sound ray of an ultrasound signal. In sound ray data $SR_k$ illustrated in FIG. 4, a white or black rectangle represents a single piece of data. The sound ray data $SR_K$ are discretized at time intervals corresponding to a sampling frequency (for example, 50 MHz) in the A/D conversion performed by the transmitting and receiving unit 3. It is illustrated in FIG. 4 that a first data position of the sound ray data $SR_K$ of a number k is set as an initial value $Z^{(k)}_0$ in a direction of the reception depth z. However, the position of the initial value can be arbitrarily set. The calculation result of the frequency analysis unit 42 is obtained as a complex number and stored in the storage unit 8.

Data groups $F_j$ (j=1, 2, . . . , K) illustrated in FIG. 4 are the amplitude data groups to be subjected to the fast Fourier transform. Generally, the number of pieces of data in the amplitude data group needs to be a power of two in order to perform the fast Fourier transform. In this sense, the amplitude data groups $F_j$ (j=2, . . . , K−1) are normal data groups since the number of pieces of data is 16 (i.e. $2^4$). However, the amplitude data groups $F_1$, $F_k$ are abnormal data groups since the number of pieces of data in $F_1$ is 9 and the number of pieces of data in $F_k$ is 12. When the fast Fourier transform is performed for the abnormal data group, a process for generating a normal amplitude data group is performed by inserting an insufficient amount of zero data. This process will be described in detail later when a process of the frequency analysis unit 42 is described (refer to FIG. 12).

Figure 5:
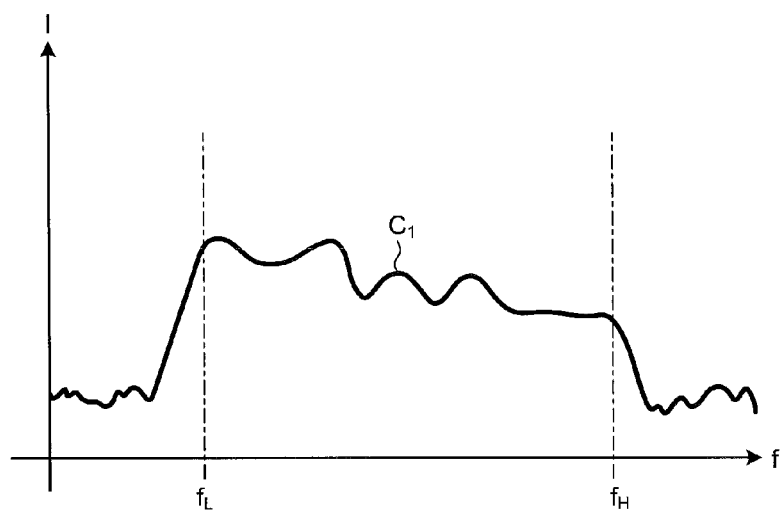
FIG. 5 is a diagram illustrating an exemplary frequency spectrum calculated by a frequency analysis unit of the ultrasound observation apparatus according to the first embodiment of the present invention.

FIG. 5 is a diagram illustrating an exemplary frequency spectrum calculated by the frequency analysis unit 42. Specifically, the "frequency spectrum" illustrated in FIG. 5 represents "a frequency distribution of intensity in a certain reception depth z" obtained by subjecting the amplitude data group to the fast Fourier transform (FFT computation). The "intensity" as used herein refers to, for example, any of parameters such as voltage of an echo signal, electric power of an echo signal, sound pressure of an ultrasound echo, and acoustic energy of an ultrasound echo, amplitude of these parameters, time integration values of these parameters, and a combination thereof. In FIG. 5, a horizontal axis represents a frequency f. A vertical axis represents decibel representation of intensity $\log_{10}(I/I_c)$ obtained by dividing an intensity I by a specific reference intensity $I_c$ (constant) and further converting it to a common logarithm. Hereinafter, in order to simplify the description in FIG. 5 and the subsequent drawings, the intensity in the form of the decibel representation is also simply referred to as I. In FIG. 5, the reception depth z is constant. In the first embodiment, a curved line and a straight line are formed by a set of discrete points.

In a frequency spectrum $C_1$ illustrated in FIG. 5, a lower limit frequency $f_L$ and an upper limit frequency $f_H$ of a frequency band used in the subsequent arithmetic operations are parameters that are determined based on, for example, a frequency band of the ultrasound transducer 21 and a frequency band of a pulse signal transmitted by the transmitting and receiving unit 3. For example, $f_L$=3 MHz and $f_H$=10 MHz are satisfied. Hereinafter, a frequency band defined in accordance with the lower frequency $f_L$ and the upper frequency $f_H$ will be referred to as a "frequency band F".

Generally, the frequency spectrum exhibits different tendencies depending on attributes of tissues scanned with the ultrasound. This is because the frequency spectrum correlates with the size of a scatterer that scatters the ultrasound, number density of the scatterer, and acoustic impedance or the like. In the first embodiment, the "attribute" represents, for example, a malignant tumor tissue, a benign tumor tissue, an endocrine tumor tissue, a mucinous tumor tissue, a normal tissue, and a vascular channel.

The feature calculation unit 43 has an attenuation correction unit 431 and an approximation unit 432. The attenuation correction unit 431 performs the attenuation correction process for correcting the influence of the attenuation of the ultrasound that depends on the reception depth and the frequency of the ultrasound. The approximation unit 432 calculates an approximation expression of the frequency spectrum after the attenuation correction by means of regression analysis.

Figures 6, 7:
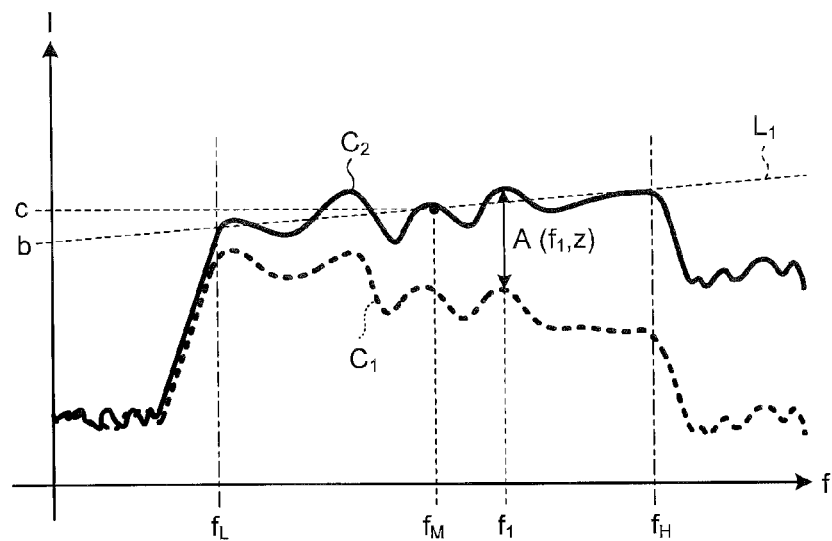
FIG. 6 is a diagram schematically illustrating an outline of a process performed by a feature calculation unit of the ultrasound observation apparatus according to the first embodiment of the present invention.
FIG. 7 is a diagram schematically illustrating a shape of each frequency spectrum obtained when the frequency spectrum that depends on the presence or absence of a contrast agent and the presence or absence of attenuation correction is regarded as a function of a frequency.

FIG. 6 is a diagram schematically illustrating an outline of the process performed by the feature calculation unit 43. FIG. 6 provides an exemplary case where the feature of the frequency spectrum $C_1$ illustrated in FIG. 5 are calculated. First, the attenuation correction unit 431 performs, for the frequency spectrum $C_1$, such correction (I (f,z)→I (f,z)+A (f,z)) as to add an attenuation amount A (f,z) of formula (1) to the corresponding intensity I (f,z) in every frequency f. The attenuation amount A (f,z) of the ultrasound is attenuation that occurs while the ultrasound is reciprocating between the reception depth zero and the reception depth z, and defined as a change in the intensity (difference in the decibel representation) before and after the reciprocation. It is empirically known that the A (f,z) is proportional to the frequency in a uniform tissue, and the A (f,z) is given by formula (1) assuming that a proportional coefficient is α.

$$A(f,z)=2\alpha z f \quad (1)$$

In the formula, α is called an attenuation factor. In addition, z is the reception depth of the ultrasound, and f is the frequency.

In a case where an object as an observation target is a living body, a specific value of the attenuation factor α is 0.0 to 1.0 (dB/cm/MHz) and more preferably 0.3 to 0.7 (dB/cm/MHz), which is defined in accordance with a portion of the living body. For example, in a case where an object as an observation target is a pancreas, α might be defined as α=0.6 (dB/cm/MHz). In the first embodiment, the value of the attenuation factor α may be configured to be capable of being set or changed in response to input from the input unit 6.

A frequency spectrum $C_2$ illustrated in FIG. 6 is a new frequency spectrum that is obtained as the result of correcting the influence of the attenuation accompanying the propagation of the ultrasound by means of the attenuation correction process.

The approximation unit 432 performs the regression analysis for the frequency spectrum $C_2$ in the frequency band F to approximate the frequency spectrum $C_2$ with a linear expression (regression line), thereby calculating the feature. The feature calculated here are a slope a and an intercept b of a regression line $L_1$ illustrated in FIG. 6, and a mid-band fit $c=af_M+b$, which is a value on the regression line in a center frequency $f_M=(f_L+f_H)/2$ of the frequency band F.

Among the three features, the slope a correlates with the size of the scatterer of the ultrasound wave. It is generally considered that the greater the scatterer is the lesser value the slope has. The intercept b correlates with the size of the scatterer, the difference in the acoustic impedance, and the number density (concentration) of the scatterer or the like. Specifically, it is considered that the greater the scatterer is the greater value the intercept b has, the greater the difference in the acoustic impedance is the greater value the intercept b has, and the greater the number density (concentration) of the scatterer is the greater value the intercept b has. The mid-band fit c is an indirect parameter derived from the slope a and the intercept b, and gives the intensity of the spectrum in the center of the effective frequency band. Therefore, it is considered that the mid-band fit c correlates with the brightness of the B-mode image to some extent in addition to the size of the scatterer, the difference in the acoustic impedance, and the number density of the scatterer. The approximation expression calculated by the approximation unit 432 is not limited to the linear expression, and a polynomial expression with a higher-order expression can also be employed.

As the feature calculated by the feature calculation unit 43, it is also possible to apply a statistic of the slope a, the intercept b, and the mid-band fit c calculated by the approximation unit 432 in a plurality of unit areas (also referred to as discrimination windows) defined within an area of interest. Examples of such a statistic include an average, a standard deviation, a variance, and entropy.

The determination unit 44 compares a shape of the frequency spectrum after the attenuation correction with a shape of a predetermined reference spectrum to determine the presence or absence of the contrast agent. Specifically, the determination unit 44 compares the shape of the frequency spectrum after the attenuation correction with the shape of the reference spectrum using a known method such as pattern matching. When the shapes of both spectra coincide, the determination unit 44 determines that the contrast agent is present in the specimen. When the determination unit 44 performs the comparison between the shapes, the determination unit 44 calculates, for example, any of a sum of squared difference (SSD), a sum of absolute difference (SAD), and a normalized cross-correlation (NCC) as the degree of similarity of the shapes. When a value of the degree of similarity is equal to or greater than a predetermined threshold value, the determination unit 44 determines that the shape of the frequency spectrum coincides with the shape of the reference spectrum, namely, the contrast agent is present in the specimen.

Hereinafter, the reference spectrum will be described. FIG. 7 is a diagram schematically illustrating the shape of each frequency spectrum obtained when the frequency spectrum that depends on the presence or absence of the contrast agent and the presence or absence of the attenuation correction is regarded as a function of a frequency. The shape of the frequency spectrum in the presence of the contrast agent significantly differs from that in the absence of the contrast agent, and the shape of the frequency spectrum before the attenuation correction also significantly differs from that after the attenuation correction.

In the presence of the contrast agent, the frequency spectrum has a large high frequency (harmonic) component. Therefore, waveforms of frequency spectra $C_{21}$, $C_{22}$ in the presence of the contrast agent are formed by adding waveforms of the high frequency components to respective waveforms of frequency spectra $C_{11}$, $C_{12}$ in the absence of the contrast agent. In this case, it is considered that the waveform of the frequency spectrum in the presence of the contrast agent is hardly affected by a tissue characteristic of a specimen.

In comparison with the waveforms of the frequency spectra $C_{11}$ and $C_{21}$ before the attenuation correction, respectively, the waveforms of the frequency spectra $C_{12}$ and $C_{22}$ after the attenuation correction each have such a shape that the high frequency component is especially largely corrected. Although the waveforms of the frequency spectra $C_{12}$ and $C_{22}$ both rise toward the right owing to the effect of the attenuation correction as compared with the waveforms before the attenuation correction, the frequency spectrum $C_{22}$ has a greater intensity and a greater rate of increase in the intensity (slope rising toward the right).

The frequency spectrum $C_{22}$ that is the frequency spectrum in the presence of the contrast agent and the frequency spectrum after the attenuation correction is stored in a reference spectrum information storage unit 81 of the storage unit 8 which will be described later as the frequency spectrum to be used as a reference when the determination unit 44 determines the presence or absence of the contrast agent, namely, as the reference spectrum.

The frequency spectrum $C_{12}$ can also be applied as the reference spectrum. In this case, when the degree of similarity between the shape of the frequency spectrum after the attenuation correction and the shape of the reference spectrum is high, the determination unit 44 determines that the contrast agent is not present in the specimen.

The image processing unit 5 has a B-mode image data generating unit 51 and a feature image data generating unit 52. The B-mode image data generating unit 51 generates B-mode image data from an echo signal. The feature image data generating unit 52 generates feature image data that cause visual information related to the feature calculated by the feature calculation unit 43 to be displayed in a display pattern that differs depending on the presence or absence of the contrast agent in the specimen.

The B-mode image data generating unit 51 performs, for a digital signal, a signal process using a known technique such as a bandpass filter, logarithmic conversion, a gain process, and a contrast process, and performs, for the digital signal, for example, decimation of data in accordance with a data step width defined in accordance with a display range of an image in the display unit 7. The B-mode image data generating unit 51 thus generates the B-mode image data. The B-mode image is a grayscale image in which values of red (R), green (G), and blue (B), which are variables to be used when an RGB color system is employed as a color space, coincide with one another.

The feature image data generating unit 52 generates the feature image data by superimposing the visual information related to the feature calculated by the feature calculation unit 43 on each pixel of an image in the B-mode image data. For example, the feature image data generating unit 52 is configured such that a pixel area corresponding to a data amount of a single amplitude data group $F_j$ (j=1, 2, . . . , K) illustrated in FIG. 4 is assigned visual information corresponding to the feature of the frequency spectrum calculated from the amplitude data group $F_j$. The feature image data generating unit 52 generates a feature image, for example, by associating a color phase as the visual information with any one of the above-mentioned slope a, intercept b, and mid-band fit c. The feature image data generating unit 52 may be configured to generate the feature image data by associating the color phase with one of the two features selected from among the slope a, the intercept b, and the mid-band fit c, and associating light and darkness with the other.

Examples of the visual information related to the feature include variables of a color space constituting a predetermined color system such as a color phase, colorfulness, brightness, a brightness value, red (R), green (G), and blue (B). In this case, the feature image data generating unit 52 changes, depending on the presence or absence of the contrast agent in the specimen, the assignment of the visual information to each type of the feature to change hue of an image as a display pattern.

The feature image data generating unit 52 adjusts brightness of the entire feature image independently of a gain for the B-mode image. The feature image data generating unit 52 also adjusts a brightness difference in the feature image independently of a contrast for the B-mode. The feature image data generating unit 52 also adjusts image quality using a table that is the same as a brightness information table for the B-mode image. The feature image data generating unit 52 also adjusts gamma of the feature image independently of gamma for the B-mode. These adjustment values can be set in accordance with the type of the ultrasound probe 2.

The storage unit 8 has the reference spectrum information storage unit 81 and a parameter information storage unit 82. The reference spectrum information storage unit 81 stores therein information about the reference spectrum with which the shape of the frequency spectrum calculated by the computation unit 4 is compared. The parameter information storage unit 82 stores therein information about a parameter that is set depending on the presence or absence of the contrast agent.

The reference spectrum information storage unit 81 stores therein the information about the reference spectrum to be referred to when the determination unit 44 determines the presence or absence of the contrast agent. The reference spectrum information includes the result of calculating the reference spectrum and information about the shape of the like of the reference spectrum. An example of the reference spectrum includes the frequency spectrum $C_{22}$ illustrated in FIG. 7.

The parameter information storage unit 82 stores therein parameters for various processes which are set in the presence of the contrast agent and parameters for various processes which are set in the absence of the contrast agent. Specific examples of the parameters include parameters for the gain, the contrast, the STC correction, the amplification correction, and the attenuation correction or the like.

The storage unit 8 also stores therein, in addition to the above-mentioned items, for example, information required for the amplification process (relation between the amplification factor and the reception depth illustrated in FIG. 2), information required for the amplification correction process (relation between the amplification factor and the reception depth illustrated in FIG. 3), information required for the attenuation correction process (refer to formula (1)), and information of a window function (such as Hamming, Hanning, and Blackman) required for the frequency analysis process.

The storage unit 8 also stores therein an operation program for executing a method for operating the ultrasound observation apparatus 1. The operation program can also be recorded in a computer-readable recording medium such as a hard disc, a flash memory, a CD-ROM, a DVD-ROM, and a flexible disc to be distributed widely. Various types of programs may be recorded in the recording medium or the like when a computer or the recording medium is shipped as a product. Alternatively, the various types of programs may be downloaded via a communication network to be recorded in the recording medium or the like.

The storage unit 8 having the above-mentioned configuration is realized by using, for example, a read only memory (ROM) on which the various types of programs or the like are installed in advance, and a random access memory (RAM) that stores therein arithmetic parameters and data or the like for each process. The above-mentioned various types of programs can also be downloaded and obtained via a communication network. The communication network as used herein is realized by, for example, whether wired or wireless, an existing public line network, a local area network (LAN), and a wide area network (WAN) or the like.

The control unit 9 has a parameter setting unit 91 that sets a parameter based on the determination result of the determination unit 44 about the presence or absence of the contrast agent. When the determination result of the determination unit 44 has changed from a determination result immediately before the determination result of the determination unit 44, the parameter setting unit 91 outputs a setting change signal that changes the setting of the parameter to the transmitting and receiving unit 3, the computation unit 4, and the image processing unit 5. The transmitting and receiving unit 3, the computation unit 4, and the image processing unit 5 refer to the parameter information storage unit 82 to execute the various processes using the parameters with the changed settings.

The control unit 9 is realized by using a central processing unit (CPU) having arithmetic and control functions and various types of arithmetic circuits or the like. The control unit 9 reads, from the storage unit 8, the various types of programs including the information stored and contained in the storage unit 8 and the operation program for the ultrasound observation apparatus 1 to execute the various arithmetic processes related to the method for operating the ultrasound observation apparatus 1. The control unit 9 thus manages and controls the ultrasound observation apparatus 1. The control unit 9 and the computation unit 4 can also be configured using a common CPU or the like.

Figure 8:
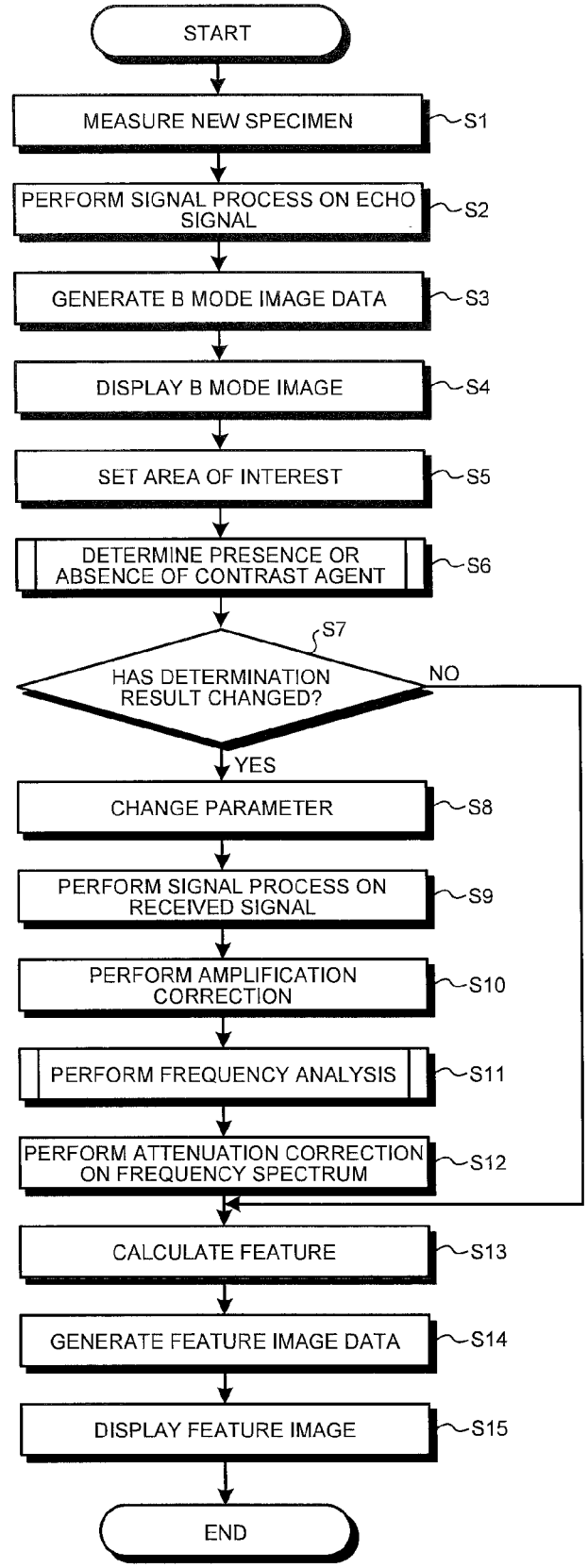
FIG. 8 is a flowchart illustrating an outline of a process performed by the ultrasound observation apparatus according to the first embodiment of the present invention.

FIG. 8 is a flowchart illustrating an outline of a process performed by the ultrasound observation apparatus 1 having the above-mentioned configuration. First, the ultrasound observation apparatus 1 measures a new specimen using the ultrasound probe 2 (step S1). Specifically, the ultrasound transducer 21 of the ultrasound probe 2 converts electrical pulse signals to ultrasound pulses and sequentially transmits the ultrasound pulses to the specimen. Each ultrasound pulse is reflected from the specimen, whereby an ultrasound echo is generated. The ultrasound transducer 21 converts the ultrasound echo to an electrical echo signal. In this case, a frequency band of the pulse signal is preferably widened so as to substantially cover a linear response frequency band for electroacoustic conversion of the pulse signal to the ultrasound pulse in the ultrasound transducer 21. As a result, an accurate approximation can be performed in an approximation process for the frequency spectrum which will be described later.

The received signal processing unit 32 receives the electrical echo signal from the ultrasound probe 2 and performs the predetermined signal process on the echo signal (step S2). The received signal processing unit 32 performs the signal process such as the amplification (STC correction) of the echo signal based on the relation between the amplification factor and the reception depth as illustrated in FIG. 2, the filtering, the A/D conversion, and the delay addition. In this case, a frequency band for the various processes for the echo signal in the received signal processing unit 32 is preferably widened so as to substantially cover a linear response frequency band for acoustoelectric conversion of the ultrasound echo to the echo signal by the ultrasound transducer 21. This can also contribute to the accurate approximation performed in the approximation process for the frequency spectrum which will be described later.

Next, the B-mode image data generating unit 51 generates B-mode image data using the echo signal amplified by the received signal processing unit 32 (step S3). After that, the control unit 9 causes the display unit 7 to display a B-mode image corresponding to the generated B-mode image data (step S4).

After step S4, the control unit 9 sets an area of interest to be displayed in a feature image based on a signal for setting the area of interest, input of which has been received by the input unit 6 (step S5). As the area of interest, it is possible to set an area of interest for observation and an area of interest for calculation that is used for performing calculation within this area of interest. A boundary of these areas of interest is displayed, for example, in white. The area of interest for calculation is displayed, for example, in a circular shape. The area of interest to be calculated can be changed between the area of interest for calculation and the entire area of interest for observation in response to the input from the input unit 6.

Figure 9:
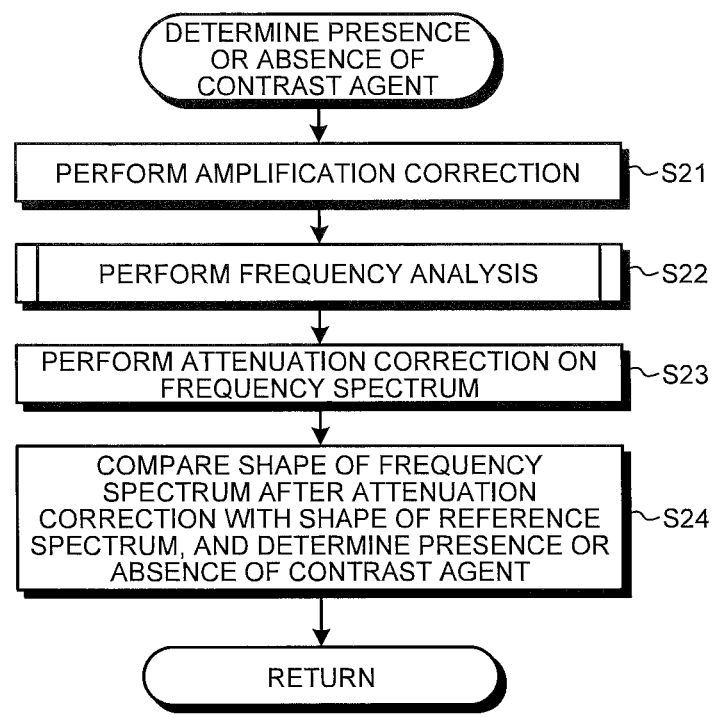
FIG. 9 is a flowchart illustrating an outline of a process for determining the presence or absence of a contrast agent performed by the ultrasound observation apparatus according to the first embodiment of the present invention.

After that, the ultrasound observation apparatus 1 determines the presence or absence of a contrast agent in an ultrasound signal (step S6). FIG. 9 is a flowchart illustrating an outline of a process for determining the presence or absence of the contrast agent performed by the ultrasound observation apparatus 1. Hereinafter, the process for determining the presence or absence of the contrast agent will be described with reference to FIG. 9.

First, the amplification correction unit 41 performs the amplification correction for a signal output from the transmitting and receiving unit 3 so that the amplification factor is constant regardless of the reception depth (step S21). At this time, the amplification correction unit 41 performs the amplification correction based on, for example, the relation between the amplification factor and the reception depth as illustrated in FIG. 3.

After that, the frequency analysis unit 42 calculates a frequency spectrum by performing the frequency analysis by means of the FFT computation (step S22). The frequency analysis process will be described in detail later.

Next, the attenuation correction unit 431 performs the attenuation correction on the frequency spectrum calculated by the frequency analysis unit 42 (step S23). The attenuation correction unit 431 obtains a new frequency spectrum by performing, for all the frequencies f, the correction process that adds the attenuation amount A of the above-mentioned formula (1) to the intensity I. As a result, it is possible to obtain the frequency spectrum (for example, the frequency spectrum $C_2$ illustrated in FIG. 6) in which contribution of the attenuation accompanying the propagation of the ultrasound is reduced.

After that, the determination unit 44 compares a shape of the frequency spectrum after the attenuation correction with a shape of a reference spectrum stored in the reference spectrum information storage unit 81, and determines the presence or absence of the contrast agent in the specimen based on the degree of similarity of the shapes (step S24). The control unit 9 writes the determination result of the determination unit 44 to the storage unit 8 and causes the storage unit 8 to store therein the determination result. The storage unit 8 stores therein the determination result at least until the next determination is performed by the determination unit 44. After step S24, the ultrasound observation apparatus 1 returns to the main routine to proceed to step S7.

In step S7, the parameter setting unit 91 compares the latest determination result in the above-mentioned step S24 with the latest determination result (i.e. preceding determination result) stored in the storage unit 8. When the determination result of the determination unit 44 has changed from the preceding determination result (step S7: Yes), the parameter setting unit 91 changes a parameter (step S8). When the determination process in step S6 is the first determination process, the parameter setting unit 91 performs the comparison assuming that the preceding determination result is "in the absence of the contrast agent".

After that, the ultrasound observation apparatus 1 executes the respective processes using the changed parameter. The processes include the signal process on the received signal (step S9), the amplification correction (step S10), the frequency analysis (step S11), and the attenuation correction on the frequency spectrum (step S12). The processes of steps S9 to S12 respectively correspond to the above-mentioned processes of steps S2, S21 to S23 except for a value of the parameter.

Next, the approximation unit 432 performs the regression analysis for the frequency spectrum after the attenuation correction (corrected frequency spectrum) in a predetermined frequency band to approximate the frequency spectrum with a linear expression, thereby calculating feature (step S13). Examples of the feature to be calculated include the above-mentioned slope a, intercept b, and mid-band fit c.

The feature image data generating unit 52 generates feature image data by, for example, superimposing a color phase as visual information that is based on the feature on each pixel in the B-mode image data generated by the B-mode image data generating unit 51 (step S14).

Figure 10:
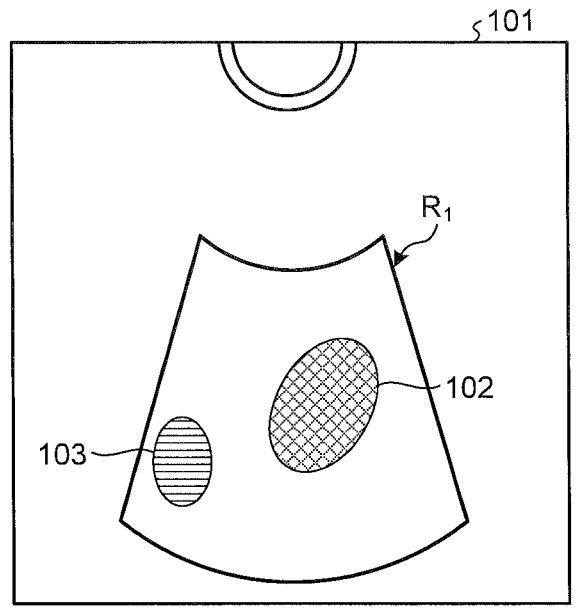
FIG. 10 is a diagram illustrating an exemplary display of a feature image in a display unit.
Figure 11:
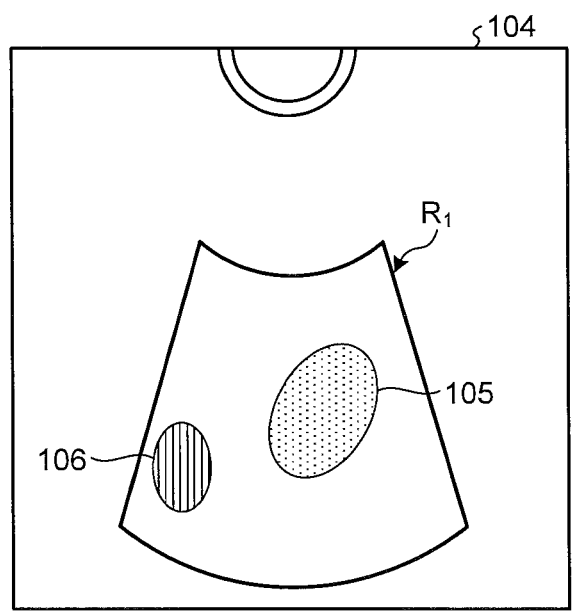
FIG. 11 is a diagram illustrating an exemplary display (first example) of a feature image displayed on the display unit when a parameter different from that of FIG. 10 is set.

After that, the display unit 7 displays, under the control of the control unit 9, a feature image corresponding to the feature image data generated by the feature image data generating unit 52 (step S15). FIGS. 10 and 11 are diagrams illustrating exemplary displays of feature images displayed on the display unit 7 when parameters different from each other depending on the presence or absence of the contrast agent are set in the same portion of the specimen. A feature image 101 illustrated in FIG. 10 has, within an area of interest $R_1$, display areas 102, 103 to which items of visual information related to the feature are added and displayed. The display areas 102, 103 correspond to the areas set as the areas of interest to be calculated. A feature image 104 illustrated in FIG. 11 is configured such that items of visual information added to display areas 105, 106 respectively corresponding to the display areas 102, 103 of the feature image 101 are respectively different from the items of the visual information added to the display areas 102, 103 of the feature image 101 illustrated in FIG. 10. In other words, assignment of the visual information to the feature in FIG. 10 is different from that in FIG. 11. In FIGS. 10 and 11, the difference in the visual information is schematically represented by the difference in the pattern. Such visual information may be the color phase, the colorfulness, the brightness, or an appropriate combination of these variables of the color space.

When the display unit 7 displays a feature image, a B-mode image corresponding to the feature image may be displayed side by side.

In step S7, when the determination result of the determination unit 44 has not changed from the preceding determination result (step S7: No), the ultrasound observation apparatus 1 does not change the parameter and proceeds to the feature calculation process in step S13.

Figure 12:
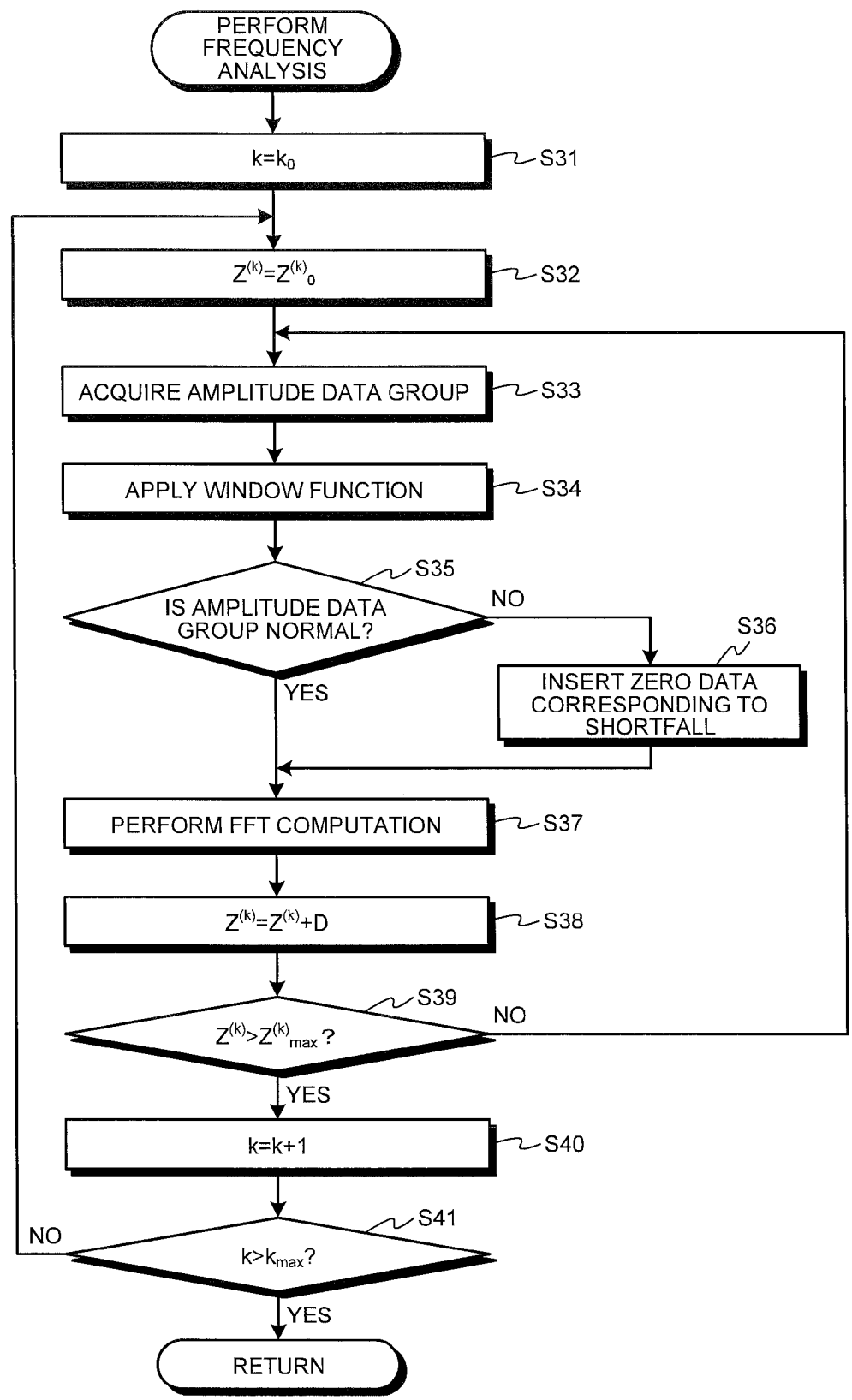
FIG. 12 is a flowchart illustrating an outline of a process performed by the frequency analysis unit of the ultrasound observation apparatus according to the first embodiment of the present invention.

FIG. 12 is a flowchart illustrating an outline of the frequency analysis process in step S11 and of FIG. 8 and step S22 of FIG. 9. In the frequency analysis process, the frequency analysis unit 42 calculates a frequency spectrum by analyzing a frequency of a digital RF signal generated based on an echo signal using a parameter that differs depending on the presence or absence of a contrast agent in a specimen. Hereinafter, the frequency analysis process will be described in detail with reference to FIG. 12.

First, the frequency analysis unit 42 sets a counter k identifying a sound ray to be analyzed to $k_0$ (step S31).

Next, the frequency analysis unit 42 sets an initial value $Z^{(k)}_0$ of a data position (corresponding to reception depth) $Z^{(k)}$ representing a series of data groups (amplitude data groups) that is obtained for the FFT computation (step S32). For example, as mentioned above, it is illustrated in FIG. 4 that the first data position of the sound ray $SR_k$ is set as the initial value $Z^{(k)}_0$.

After that, the frequency analysis unit 42 acquires the amplitude data group to which the data position $Z^{(k)}$ belongs (step S33), and applies a window function stored in the storage unit 8 to the acquired amplitude data group (step S34). By causing the window function to act on the amplitude data group in the above-mentioned manner, it is possible to avoid discontinuity of the amplitude data group at the boundary and prevent generation of an artifact.

Next, the frequency analysis unit 42 determines whether the amplitude data group with the data position $Z^{(k)}$ is a normal data group (step S35). As described with reference to FIG. 4, the number of pieces of data in the amplitude data group needs to be a power of two. Hereinafter, the number of pieces of data in the amplitude data group is assumed to be $2^n$ (n is a positive integer). In the first embodiment, the data position $Z^{(k)}$ is set so as to be located, as much as possible, in the center of the amplitude data group to which $Z^{(k)}$ belongs. Specifically, since the number of pieces of data in the amplitude data group is $2^n$, $Z^{(k)}$ is set at a $2^n/2$ (i.e. $2^{n-1}$)-th position near the center of the amplitude data group. In other words, it is meant by the normal amplitude data group that $2^{n-1}-1$ (i.e. assumed to be N) pieces of data are present ahead of the data position $Z^{(k)}$ and $2^{n-1}$ (i.e. assumed to be M) pieces of data are present behind the data position $Z^{(k)}$. In the example illustrated in FIG. 4, the amplitude data groups $F_2$, $F_3$ are both normal. In the example illustrated in FIG. 4, n=4 (N=7, M=8) is satisfied.

When the amplitude data group with the data position $Z^{(k)}$ is normal as the result of the determination in step S35, (step S35: Yes), the frequency analysis unit 42 proceeds to step S37 which will be described later.

When the amplitude data group with the data position $Z^{(k)}$ is not normal as the result of the determination in step S35 (step S35: No), the frequency analysis unit 42 generates a normal amplitude data group by inserting zero data corresponding to shortfall (step S36). The window function has acted on the amplitude data group determined to be not normal in step S35 (for example, the amplitude data groups $F_1$, $F_k$ in FIG. 4) before the zero data are added. Therefore, the discontinuity of the data does not occur even if the zero data are inserted into the amplitude data group. After step S36, the frequency analysis unit 42 proceeds to step S37 which is described later.

In step S37, the frequency analysis unit 42 performs the FFT computation using the amplitude data group to obtain a frequency spectrum which is a frequency distribution of amplitude (step S37). As a result, the frequency spectrum having, for example, the frequency spectrum $C_1$ illustrated in FIG. 5 can be obtained.

Next, the frequency analysis unit 42 changes the data position $Z^{(k)}$ with a step width D (step S38). The step width D is stored in the storage unit 8 in advance. In the example of illustrated in FIG. 4, D=15 is satisfied. The step width D desirably coincides with a data step width that is used when the B-mode image data generating unit 51 generates the B-mode image data. In a case where an arithmetic operation amount in the frequency analysis unit 42 needs to be reduced, a value greater than the data step width may be set as the step width D.

After that, the frequency analysis unit 42 determines whether the data position $Z^{(k)}$ is greater than a maximum value $Z^{(k)}_{max}$ in the sound ray $SR_k$ (step S39). When the data position $Z^{(k)}$ is greater than the maximum value $Z^{(k)}_{max}$ (step S39: Yes), the frequency analysis unit 42 increases the counter k by one (step S40). This means that the process is transferred to the next sound ray. On the other hand, when the data position $Z^{(k)}$ is equal to or less than the maximum value $Z^{(k)}_{max}$ (step S39: No), the frequency analysis unit 42 returns to step S33. In the above-mentioned way, the frequency analysis unit 42 performs, for the sound ray $SR_k$, the FFT computation on $[(Z^{(k)}_{max}-Z^{(k)}_0+1)/D+1]$ amplitude data groups. In this case, [X] represents a maximum integer not exceeding X.

After step S40, the frequency analysis unit 42 determines whether the counter k is greater than a maximum value $k_{max}$ (step S41). When the counter k is greater than a maximum value $k_{max}$ (step S41: Yes), the frequency analysis unit 42 ends a series of FFT processes. On the other hand, when the counter k is equal to or less than $k_{max}$ (step S41: No), the frequency analysis unit 42 returns to step S32.

In the above-mentioned way, the frequency analysis unit 42 performs a plurality of FFT computations on the respective ($k_{max}-k_0+1$) sound rays within the area of interest.

According to the first embodiment of the present invention described above, the frequency spectrum is calculated by analyzing the frequency of the ultrasound within the area of interest set in the specimen using the parameter that differs depending on the presence or absence of the contrast agent, and the feature image data are generated using the feature of the frequency spectrum, whereby the feature image can be appropriately generated even when the contrast agent is used.

In addition, according to the first embodiment, the information of the known frequency spectrum containing the contrast agent is stored as the reference spectrum information, and the presence or absence of the contrast agent is determined using the frequency spectrum calculated by the frequency analysis unit and the reference spectrum information, whereby the presence or absence of the contrast agent can be accurately determined.

Modifications

Figure 13:
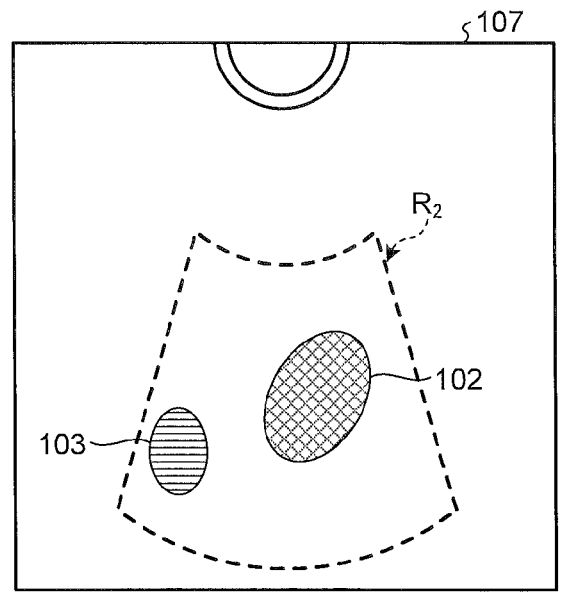
FIG. 13 is a diagram illustrating an exemplary display (second example) of a feature image displayed on the display unit when a parameter different from that of FIG. 10 is set.

FIG. 13 is a diagram illustrating another exemplary display (second example) of a feature image displayed on the display unit 7 when a parameter different from that of the feature image 101 illustrated in FIG. 10 is set. A feature image 107 illustrated in FIG. 13 is configured such that a display pattern of a boundary of an area of interest is different from that of the feature image 101. Specifically, an area of interest $R_2$ in the feature image 107 is displayed with a broken line. This allows a user to recognize that the feature image 107 has been generated using a parameter different from that of the feature image 101.

Figure 14:
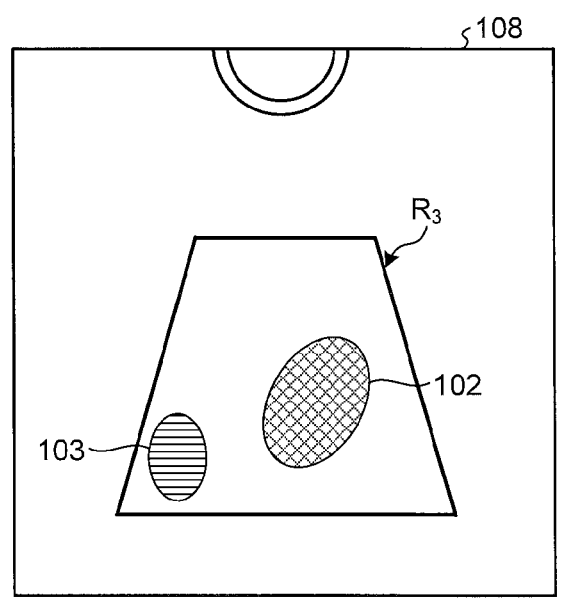
FIG. 14 is a diagram illustrating another exemplary display (third example) of a feature image displayed on the display unit when a parameter different from that of the feature image illustrated in FIG. 10 is set.

FIG. 14 is a diagram illustrating another exemplary display (third example) of a feature image displayed on the display unit 7 when a parameter different from that of the feature image 101 illustrated in FIG. 10 is set. A feature image 108 illustrated in FIG. 14 is configured such that a display pattern of a boundary of an area of interest is different from that of the feature image 101. Specifically, an area of interest $R_3$ in the feature image 108 is displayed in a form different from that of the area of interest $R_1$ in the feature image 101. This allows a user to recognize that the feature image 108 has been generated using a parameter different from that of the feature image 101.

Figure 15:
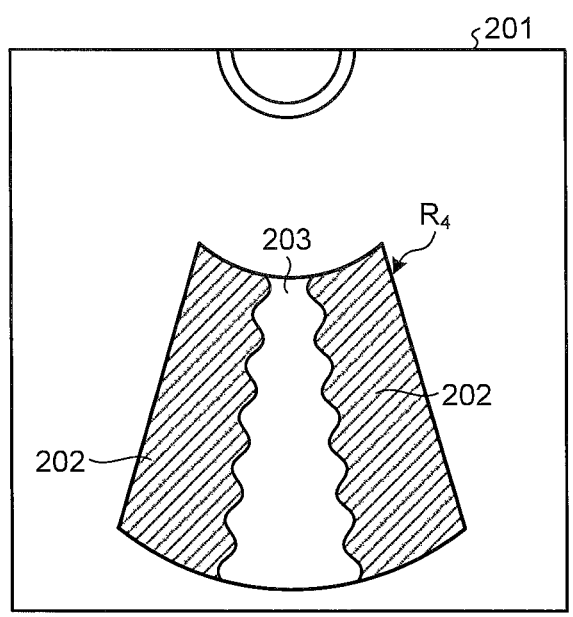
FIG. 15 is a diagram illustrating another exemplary display of a feature image displayed on the display unit in the presence of a contrast agent.

FIG. 15 is a diagram illustrating another exemplary display of a feature image displayed on the display unit 7 in the presence of a contrast agent. A feature image 201 illustrated in FIG. 15 has, within an area of interest $R_4$, a superimposed display area 202 in which a B-mode image and a feature image are superimposed and displayed, and a B-mode display area 203 in which only a B-mode image is displayed. In FIG. 15, the superimposed display area 202 is schematically depicted in oblique stripes.

The feature image data generating unit 52 changes, in accordance with a brightness value of each pixel in B-mode image data, how to combine visual information related to feature with the B-mode image data. For example, the feature image data generating unit 52 generates feature image data by setting, as the B-mode display area, a high echo area (first area) with brightness equal to or greater than a predetermined threshold value while setting, as the superimposed display area, a low echo area (second area) with brightness less than the threshold value. By displaying such a feature image, only the B-mode image is displayed in the high echo area in which the contrast agent is highly possibly included. This can improve the visibility of a flow of the contrast agent.

Instead of setting the high echo area as the B-mode display area and the low echo area as the superimposed display area, the high echo area may be set as the superimposed display area and the low echo area may be set as the B-mode display area. In addition, a rate of superimposing the visual information of the feature on the B-mode may be changed in accordance with the brightness.

Second Embodiment

A second embodiment of the present invention is characterized in that the presence or absence of a contrast agent is determined by comparing a shape of a frequency spectrum before the attenuation correction with a shape of a reference spectrum which is a known frequency spectrum before the attenuation correction.

The configuration of the ultrasound observation apparatus according to the second embodiment is the same as the configuration of the ultrasound observation apparatus 1 described in the first embodiment. However, the reference spectrum information storage unit 81 of the storage unit 8 stores therein, as the reference spectrum information, information about the known frequency spectrum before the attenuation correction in the presence of the contrast agent.

Figure 16:
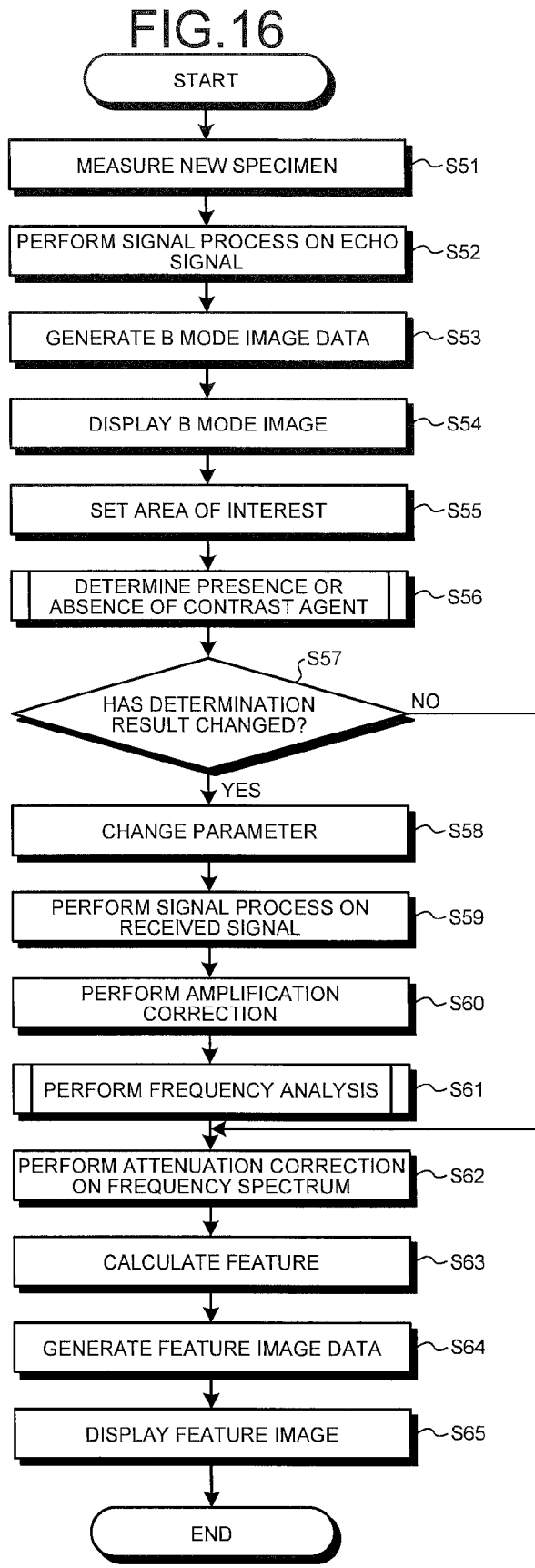
FIG. 16 is a flowchart illustrating an outline of a process performed by an ultrasound observation apparatus according to a second embodiment of the present invention.

FIG. 16 is a flowchart illustrating an outline of a process performed by the ultrasound observation apparatus 1 according to the second embodiment. In the flowchart illustrated in FIG. 16, processes of steps S51 to S55 respectively correspond to the processes of steps S1 to S5 (refer to FIG. 8) described in the first embodiment.

Figures 17, 18:
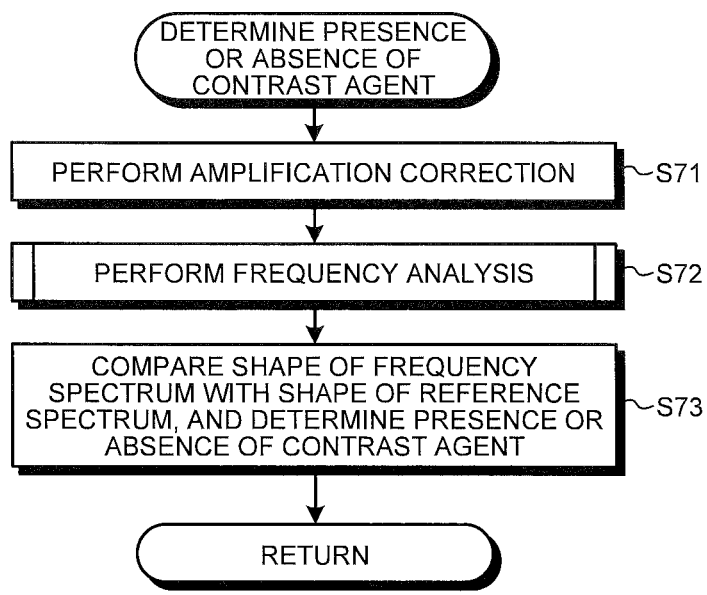
FIG. 17 is a flowchart illustrating an outline of a process for determining the presence or absence of a contrast agent performed by the ultrasound observation apparatus according to the second embodiment of the present invention.
FIG. 18 is a diagram illustrating a relation between the presence or absence of a contrast agent and a frequency band stored in a storage unit of the ultrasound observation apparatus according to the second embodiment of the present invention.

After step S55, the ultrasound observation apparatus 1 determines the presence or absence of a contrast agent in an ultrasound signal (step S56). FIG. 17 is a flowchart illustrating an outline of a process for determining the presence or absence of a contrast agent performed by the ultrasound observation apparatus 1. Hereinafter, the process for determining the presence or absence of the contrast agent will be described with reference to FIG. 17.

First, the amplification correction unit 41 performs the amplification correction on a signal output from the transmitting and receiving unit 3 such that the amplification factor is constant regardless of the reception depth (step S71).

After that, the frequency analysis unit 42 calculates a frequency spectrum by performing the frequency analysis by means of the FFT computation (step S72). The detail of the frequency analysis process is the same as that described in the first embodiment (refer to FIG. 12).

After that, the determination unit 44 compares a shape of the frequency spectrum with a shape of a reference spectrum stored in the reference spectrum information storage unit 81, and determines the presence or absence of the contrast agent in the specimen based on the degree of similarity of the shapes (step S73). The control unit 9 writes the determination result of the determination unit 44 to the storage unit 8 and causes the storage unit 8 to store therein the determination result. After step S73, the ultrasound observation apparatus 1 returns to the main routine to proceed to step S57.

In step S57, the parameter setting unit 91 compares the latest determination result in the above-mentioned step S73 with the latest determination result (i.e. preceding determination result) stored in the storage unit 8. When the determination result of the determination unit 44 has changed from the preceding determination result (step S57: Yes), the parameter setting unit 91 changes a parameter (step S58). When the determination process in step S56 is the first determination process, the parameter setting unit 91 performs the comparison assuming that the preceding determination result is "in the absence of the contrast agent".

The processes of steps S59 to S65 subsequent to step S58 respectively correspond to the processes of steps S9 to S15 described in the first embodiment.

In step S57, when the determination result of the determination unit 44 has not changed from the preceding determination result (step S57: No), the ultrasound observation apparatus 1 does not change the parameter and proceeds to the attenuation correction process in step S62.

According the second embodiment of the present invention described above, a feature image can be appropriately generated even when the contrast agent is used in the same way as the first embodiment.

In addition, according to the second embodiment, the presence or absence of the contrast agent can be accurately determined in the same way as the first embodiment.

Other Embodiments

Although the embodiments for practicing the present invention have been described so far, the present invention should not be limited only by the above-mentioned embodiments. For example, a frequency band in which the frequency analysis unit 42 performs the frequency analysis may be changed depending on the presence or absence or the contrast agent. FIG. 18 is a diagram illustrating a relation between the presence or absence of the contrast agent and the frequency band stored in the storage unit 8. In a table Tb illustrated in FIG. 18, frequency bands $f_L$ to $f_H$ in the absence of the contrast agent and frequency bands $f_L'$ to $f_H'$ in the presence of the contrast agent are generally different. The frequency analysis unit 42 refers to the table Tb to perform the frequency analysis in the frequency band in accordance with the presence or absence of the contrast agent.

Instead of the process that the determination unit 44 determines the presence or absence of the contrast agent, the input unit 6 may receive input of predetermined information indicating administration of the contrast agent to the specimen, and the parameter setting unit 91 may change the parameter in response to the acceptance of the input of the information. In this case, it is possible to execute the process using an appropriate parameter in accordance with the input and display an appropriate feature image.

In addition, the determination unit 44 may compare a feature of the frequency spectrum with a feature of the reference spectrum to determine the presence or absence of the contrast agent in the specimen. In this case, information about the feature of the reference spectrum is also stored in the reference spectrum information storage unit 81.

Furthermore, the storage unit 8 can store therein a digital RF signal generated by the received signal processing unit 32 as RAW data. This storage process is only required to be executed when the input unit 6 receives input of a storage instruction signal. In this case, moreover, when the input unit 6 receives input of an image display instruction signal, the computation unit 4 is only required to read the RAW data from the storage unit 8 to execute various arithmetic processes, and the image processing unit 5 is only required to generate B-mode image data and feature image data. As a result, an image which is the same as that at the time of measurement (in real time) can be displayed even after the measurement of the specimen is finished.

According to some embodiments, a frequency spectrum is calculated by analyzing a frequency of an ultrasound wave within an area of interest set in a specimen using a parameter that differs depending on presence or absence of a contrast agent, and feature image data is generated using a feature of the frequency spectrum, whereby a feature image can be appropriately generated even when the contrast agent is used.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasound observation apparatus comprising:
   a frequency analysis unit configured to analyze a frequency of a signal using a parameter that differs depending on presence or absence of a contrast agent in a specimen to calculate a frequency spectrum, the signal being generated based on an echo signal obtained by converting an ultrasound echo, which is an ultrasound wave transmitted to and reflected from the specimen, into an electric signal;
   a feature calculation unit configured to calculate a feature of the frequency spectrum calculated by the frequency analysis unit;
   a feature image data generating unit configured to generate feature image data for displaying visual information related to the feature calculated by the feature calculation unit in a display pattern that differs depending on the presence or absence of the contrast agent in the specimen;
   a storage unit configured to store, as reference spectrum information, information on a known frequency spectrum in the presence of the contrast agent in the specimen;
   a determination unit configured to determine the presence or absence of the contrast agent using the frequency spectrum and the reference spectrum information; and
   a control unit configured to change a setting of the parameter in accordance with a determination result by the determination unit.

2. The ultrasound observation apparatus according to claim 1, wherein
   the reference spectrum information includes a shape of the known frequency spectrum that is obtained by expressing the known frequency spectrum as a function of a frequency, and
   the determination unit is configured to compare the shape of the known frequency spectrum with a shape of the frequency spectrum calculated by the frequency analysis unit to determine the presence or absence of the contrast agent in the specimen, the shape of the frequency spectrum being obtained by expressing the frequency spectrum as a function of the frequency.

3. The ultrasound observation apparatus according to claim 1, further comprising an input unit configured to receive input of information indicating that the contrast agent has been administered to the specimen, wherein
   the control unit is configured to change the setting of the parameter when the input unit receives the input of the information.

4. The ultrasound observation apparatus according to claim 1, wherein
   the visual information is a variable of a color space, and
   the feature image data generating unit is configured to change, depending on the presence or absence of the contrast agent in the specimen, assignment of the visual information to the feature, to generate the feature image data.

5. The ultrasound observation apparatus according to claim 1, wherein
   the feature image data generating unit is configured to superimpose the visual information on B-mode image data for displaying amplitude of the echo signal having been converted into brightness, to generate the feature image data.

6. The ultrasound observation apparatus according to claim 5, wherein
   when the feature image data generating unit superimposes the visual information on the B-mode image data, the feature image data generating unit is configured to superimpose the visual information only on one of a first area with the brightness equal to or greater than a threshold value and a second area with the brightness less than the threshold value.

7. The ultrasound observation apparatus according to claim 1, further comprising a display unit configured to display a feature image corresponding to the feature image data.

8. The ultrasound observation apparatus according to claim 7, wherein
   the control unit is configured to change, depending on the presence or absence of the contrast agent in the specimen, a display pattern of an area of interest as an observation target to cause the display unit to display the feature image.

9. A method for operating an ultrasound observation apparatus that transmits an ultrasound wave to a specimen and receives an ultrasound echo reflected from the specimen to convert the ultrasound echo into an electrical echo signal, the method comprising:
   analyzing, by a frequency analysis unit, a frequency of a signal generated based on the echo signal, using a parameter that differs depending on presence or absence of a contrast agent in the specimen to calculate a frequency spectrum;
   calculating, by a feature calculation unit, a feature of the frequency spectrum;
   generating, by a feature image data generating unit, feature image data for displaying visual information related to the feature in a display pattern that differs depending on the presence or absence of the contrast agent in the specimen;
   determining, by a determination unit, the presence or absence of the contrast agent using the frequency spectrum and reference spectrum information that is information on a known frequency spectrum in the presence of the contrast agent in the specimen; and changing, by a control unit, a setting of the parameter in accordance with a result of determining the presence or absence of the contrast agent.

10. A non-transitory computer-readable recording medium with an executable program stored thereon, the program instructing an ultrasonic observation apparatus that transmits an ultrasound wave to a specimen and receives an ultrasound echo reflected from the specimen to convert the ultrasound echo into an electrical echo signal, to execute:
analyzing, by a frequency analysis unit, a frequency of a signal generated based on the echo signal, using a parameter that differs depending on presence or absence of a contrast agent in the specimen to calculate a frequency spectrum;
calculating, by a feature calculation unit, a feature of the frequency spectrum;
generating, by a feature image data generating unit, feature image data for displaying visual information related to the feature in a display pattern that differs depending on the presence or absence of the contrast agent in the specimen;
determining, by a determination unit, the presence or absence of the contrast agent using the frequency spectrum and reference spectrum information that is information on a known frequency spectrum in the presence of the contrast agent in the specimen; and
changing, by a control unit, a setting of the parameter in accordance with a result of determining the presence or absence of the contrast agent.

* * * * *